US006712853B2

(12) United States Patent
Kuslich

(10) Patent No.: US 6,712,853 B2
(45) Date of Patent: Mar. 30, 2004

(54) ANNULUS-REINFORCING BAND

(75) Inventor: Stephen D. Kuslich, Stillwater, MN (US)

(73) Assignee: Spineology, Inc., Stillwater, MN (US)

( * ) Notice: Subject to any disclaimer, the term of this patent is extended or adjusted under 35 U.S.C. 154(b) by 0 days.

(21) Appl. No.: 10/022,048

(22) Filed: Dec. 17, 2001

(65) Prior Publication Data
US 2002/0077701 A1 Jun. 20, 2002

Related U.S. Application Data
(60) Provisional application No. 60/256,014, filed on Dec. 15, 2000.

(51) Int. Cl.[7] .................................................. A61F 2/44
(52) U.S. Cl. .................................. 623/17.16; 623/17.11
(58) Field of Search ........................... 623/17.11, 17.15, 623/17.16; 606/61

(56) References Cited

U.S. PATENT DOCUMENTS

| | | | |
|---|---|---|---|
| 4,401,112 A | 8/1983 | Rezaian | 128/92 |
| 4,501,269 A | 2/1985 | Bagby | 128/92 |
| 4,743,256 A | 5/1988 | Brantigan | 623/17 |

(List continued on next page.)

FOREIGN PATENT DOCUMENTS

| | | |
|---|---|---|
| WO | 99/02108 | 1/1999 |
| WO | 00/67650 | 11/2000 |

OTHER PUBLICATIONS

*Lumbar Interbody Cage Fusion for Back PAin: An Update on The BAK (Bagby and Kuslich) System*, Kuslich S. D., Spine State of the Art Reviews 1999; 13 (2): 295–311).

*Summary of Safety and Effectiveness of the BAK Interbody Fusion System*, Food and Drug Administration (FDA) (PMA 95002), PMA Document Mail Center (HFZ–401), Center for Disease and Radiological Health, Washington DC Sept. 20, 1996, pp. 4–21.

*Granular Solids, Liquids, and Gases*, by H.M. Jaeger, S.R. Nagel and R.P. Behringer, Rev. Mod. Phys. 68, pp. 1259–1273 (1996);.

*The Tissue Origin of Mechanical Low Bck Pain and Sciatica as Identifiefd by Spinal Microsurgery*, by S. D. Kuslich, pp. 595–600, Orthop. Clin. North. Amer. 1991.

*The Bak (Bagby and Kuslich) Method of Lumbar Interbody Fusion* by Kuslich, Ulstrom, Griffith, Ahern, Dowdle, SPINE, 1998, 23:1267–1279.

*Primary Examiner*—Cary E. O'Connor
*Assistant Examiner*—Candice C. Melson
(74) *Attorney, Agent, or Firm*—Patterson, Thuente, Skaar & Christensen, P.A.

(57) ABSTRACT

A pliable band or hoop that is flexible to normal handling, but cannot stretch circumferentially once it has reached the limits of its circumferential length. The band may have a structural portal to be used for filling, or it may simply be constructed of a fabric-like material that allows a fill tube to perforate its walls to allow for filling. In the latter case, the perforated wall tends to self-seal once the fill tube is withdrawn. The band may be flat or tubular in cross-section. However, unlike a balloon, the band does not require either a bottom or a top, as we found that a top and bottom are unnecessary when using a band or hoop to enclose material injected into a reamed out intervertebral space.

31 Claims, 12 Drawing Sheets

U.S. PATENT DOCUMENTS

| | | | |
|---|---|---|---|
| 4,772,287 A | 9/1988 | Ray | 623/17 |
| 4,820,305 A | 4/1989 | Harms et al. | 623/16 |
| 4,834,757 A | 5/1989 | Bantigan | 623/17 |
| 4,878,915 A | 11/1989 | Brantigan | 623/17 |
| 4,936,848 A | 6/1990 | Bagby | 623/17 |
| 4,946,458 A | 8/1990 | Harms et al. | 606/61 |
| 5,015,247 A | 5/1991 | Michelson | 606/61 |
| 5,015,255 A | 5/1991 | Kuslich | 623/17 |
| 5,059,193 A | 10/1991 | Kuslich | 606/61 |
| 5,092,266 A | 3/1992 | Kuo | 118/425 |
| 5,192,326 A | 3/1993 | Bao et al. | 623/17 |
| 5,263,953 A | 11/1993 | Bagby | 606/61 |
| 5,331,975 A | 7/1994 | Bonutti | 128/898 |
| 5,405,391 A | 4/1995 | Henderson et al. | 623/17 |
| 5,489,307 A | 2/1996 | Kuslich | 623/17 |
| 5,489,308 A | 2/1996 | Kuslich | 623/17 |
| 5,514,180 A | 5/1996 | Heggeness et al. | 623/17 |
| 5,549,679 A | 8/1996 | Kuslich | 623/17 |
| 5,571,189 A | 11/1996 | Kuslich | 623/17 |
| 5,591,235 A | 1/1997 | Kuslich | 623/17 |
| 5,645,597 A * | 7/1997 | Krapiva | 473/377 |
| 5,669,909 A | 9/1997 | Zdeblick et al. | 606/61 |
| 5,700,291 A | 12/1997 | Kuslich et al. | 623/17 |
| 5,709,683 A | 1/1998 | Bagby | 606/61 |
| 5,720,748 A | 2/1998 | Kuslich | 606/80 |
| 5,735,899 A | 4/1998 | Schwartz et al. | 623/17 |
| 5,895,427 A | 4/1999 | Kuslich | 623/17 |
| 5,972,031 A | 10/1999 | Biedermann et al. | 623/17 |
| 6,010,502 A | 1/2000 | Bagby | 606/61 |
| 6,015,436 A | 1/2000 | Schonhoffer | 623/17 |
| 6,039,762 A * | 3/2000 | McKay | 623/17.11 |
| 6,127,597 A | 10/2000 | Beyar et al. | 623/16 |
| 6,332,894 B1 | 12/2001 | Stalcup et al. | 623/17.11 |
| 6,447,543 B1 * | 9/2002 | Studer et al. | 623/17.11 |

* cited by examiner

ANNULUS-REINFORCING BAND

CROSS-REFERENCE TO RELATED APPLICATIONS

This application claims priority from U.S. provisional application No. 60/256,014, filed Dec. 15, 2000, the entire contents of which are incorporated herein by reference.

STATEMENT REGARDING FEDERALLY SPONSORED RESEARCH

Not Applicable.

BACKGROUND OF THE INVENTION

1. Field of the Invention

This invention relates to devices that provide a means to support and/or reinforce and/or stabilize a diseased mammalian spinal intervertebral disc.

2. Description of the Related Art

It is recognized that the spinal disc consists of three parts: first, the nucleus, a central portion that is a compression-resisting cushion; second, the annulus, a peripheral rim portion that is a tension-resisting hoop; and third, the end plate, the superior and inferior borders of the disc, consisting of the up and down borders of the vertebral body bones.

Many studies have concluded that mechanical back pain is the most common and costly musculoskeletal condition affecting middle-aged humans in modem societies. Mechanical back pain may be caused by several factors, but overwhelming evidence suggests that degeneration of the spinal intervertebral disc, such as may be caused by Degenerative Disc Disease (DDD) is the most common condition causing back pain symptoms.

The inventor, in a previously published work entitled *The tissue origin of low back pain and sciatica: A report of pain response to tissue stimulation during operations on the lumbar spine using local anesthesia.* (Orthop. Clin. North Amer. 1991; 22(2):181–187.), demonstrated that the diseased disc rim or annulus is the principle pain generator responsible for mechanical back pain.

Many devices have been invented for the purpose of stabilizing and/or replacing parts of the disc in an effort to ease the pain associated with disc disease. Indeed, one of the author's prior inventions, the BAK has been used in more than 80,000 humans, with generally good results (See generally: *the Bagby and Kuslich Method of Lumbar Interbody Fusion. History, Techniques, and 2-year Follow-up Results of a United States Prospective, Multicenter Trial.* Kuslich S. D., Ulstrom C. L., Griffith S. L., Ahem J. W., Dowdle J. D., Spine 1998;23:1267–1279; *Summary of Safety and Effectiveness Of the BAK Interbody Fusion System,* Food and Drug Administration (FDA) (PMA 950002), PMA Document Mail Center (HFZ-401), Center for Disease and Radiological Health, Washington D.C., Sep. 20, 1996; and *Lumbar Interbody Cage Fusion for Back Pain: an Update on The BAK (Bagby and Kuslich) System,* Kuslich S. D., Spine: State of the Art Reviews 1999;13(2):295–311). Unfortunately, the BAK and many similarly structured rigid metallic implants suffer from several less than ideal features such as: the need to create fairly large surgical exposures, the need for fairly large entrance holes through the annulus of the disc, and the presence of fairly large volumes of metal that reduce bone graft surface contact at the end plate.

Any device that would more easily, and/or more effectively, and/or more safely treat degenerative disc disease would be useful in the management of hundreds of thousands of suffering individuals.

Previous patents involving intervertebral devices designed to treat DDD fall generally into the following four classes:

The first class includes rigid, three-dimensional geometric solid devices, either impervious or porous, that function as support struts. When placed in the area of the disc between adjacent vertebral bodies, they allow and/or encourage bone to grow through and/or around the device to cause a bony fusion between two adjacent vertebral bodies. Examples of such devices have been described in the following references:

U.S. Pat. No. 6,015,436 to Schönhöffer
U.S. Pat. No. 6,010,502 to Bagby
U.S. Pat. No. 5,972,031 to Biedermann et al.
U.S. Pat. No. 5,895,427 to Kuslich
U.S. Pat. No. 5,735,899 to Schwartz et al.
U.S. Pat. No. 5,720,748 to Kuslich
U.S. Pat. No. 5,709,683 to Bagby
U.S. Pat. No. 5,700,291 to Kuslich
U.S. Pat. No. 5,669,909 to Zdeblick
U.S. Pat. No. 5,514,180 to Heggeness et al.
U.S. Pat. No. 5,591,235 to Kuslich
U.S. Pat. No. 5,489,308 to Kuslich
U.S. Pat. No. 5,489,307 to Kuslich
U.S. Pat. No. 5,405,391 to Henderson et al.
U.S. Pat. No. 5,263,953 to Bagby
U.S. Pat. No. 5,059,193 to Kuslich
U.S. Pat. No. 5,015,255 to Kuslich
U.S. Pat. No. 5,015,247 to Michelson
U.S. Pat. No. 4,946,458 to Harms et al.
U.S. Pat. No. 4,936,848 to Bagby
U.S. Pat. No. 4,834,757 to Bantigan
U.S. Pat. No. 4,820,305 both to Harms et al.
U.S. Pat. No. 4,501,269 to Bagby
U.S. Pat. No. 4,401,112 to Rezaian The second class involves the use of semi-rigid artificial joints that allow motion in one or more planes. Examples include U.S. Pat. No. 4,759,769 to Kostuik, U.S. Pat. No. 6,039,763 to Shelokov, and commercially available examples such as the Link device or Charite Intervertebral Disc Endoprosthesis.

The third class is directed to non-rigid cushions designed to replace the nucleus of the disc. Examples of artificial discs are described in U.S. Pat. No. 4,904,260 to Ray, U.S. Pat. No. 4,772,287 to Ray and U.S. Pat. No. 5,192,326 to Boa.

Finally, the fourth class is the relatively new area of initially flexible, expandable bags or balloons that become rigid when injected with materials that can support loads. Examples include U.S. Pat. Nos. 5,571,189 and 5,549,679 to Kuslich, each of which describe expandable, porous balloons or bags, useful in stabilizing a deteriorating spinal disc. In this fourth class, a porous bag or balloon is used which is closed except for a mouth through which bone graft or other graft material is inserted. The bag is placed into a reamed out intervertebral space and is expanded by the introduction of graft material. Recent research and development in the inventor's laboratory established the fact that a thin walled band or hoop, either porous or non-porous, can be placed in the region of the annulus by means of several techniques. Such a band or bands as described in detail below effectively reinforce the annulus and thereby support spinal motion segment strain deflections resulting from stresses applied in all vector directions: rotation, flexionextension, side bending, compression and distraction. Furthermore, the inventor's experiments show that these radially applied bands or hoops can effectively contain and retain inserted or injected materials that are placed in the central region of a reamed-out disc.

The current invention teaches a technique for building and using a simple band to perform many of the functions of the prior art described above. For instance, if compared to metal cylindrical implants such as described in U.S. Pat. No. 5,015,247 to Michelson and metal-walled or plastic-walled rectangular shaped implants such as may be described in U.S. Pat. No. 4,878,915 and U.S. Pat. No. 4,743,256 both to Brantigan, the bands of this invention are softer, lighter, more pliable, and without hard sharp edges, thereby offering greater safety during passage next to delicate structures such as the great vessels or the spinal cord. Also, the completely open structure at the Polar Regions adjacent to cancellous bone of the vertebral bodies, would allow for a more intimate fit between inserted graft material and living bone. This intimacy of contact, without any intervening implant material, may reasonably lead to a faster and more complete biological ingrowth through the central portion of the implant.

It is well known that greater surface area contact between graft and living bone is conducive to higher fusion rates and conversely, lower non-union rates. Thus, the current invention provides for several unique advantages over prior art in the field of interbody fusion devices.

In addition to its uses and advantages in the form of improved interbody fusion devices, the attributes of the current invention would provide a new and potentially superior technology in two other categories of treatment for degenerative disc disease: one, soft tissue reinforcement of diseased discs, and two, disc replacement.

In regard to soft tissue reinforcement of diseased discs, several new techniques have recently become available to treat early and mid-stage disc degeneration by methods less invasive and less drastic than fusion surgery. Examples include: annular tissue modulation by heat application (See generally: Saal J. et al. North American Spine Society presentations 1999, 2000); the use of a polyester tension band placed around and between pedicle screws above and below the involved disc such as, described in U.S. Pat. No. 5,092,266 to Graf; and combined tension and distraction devices placed between pedicle screws, such as may be seen in the commercially available DyneSyS™ device from Sulzer Orthopedics Ltd. While early results from the above technologies appear promising, the current invention would obviate some of the potential dangers and drawbacks of these systems. For example:

In the case of annular tissue modulation by heat application, the current invention does not require heat. Heat can be injurious to local spinal nerves and vessels, possibly leading to paralysis or even death by hemorrhage. The current invention immediately stabilizes the annulus, rather than having to wait until the heat-damaged tissue heals and shrinks.

In the case of a polymeric tension band placed between pedicle screws above and below the involved disc, the current invention does not require the placement of pedicle screws. The placement of pedicle screws requires a significant surgical exposure with attendant bleeding and injury to local muscular, ligamentous, vascular and nervous tissues. The current invention can be installed through much smaller, microsurgical exposures that would have less likelihood of causing collateral damage.

In the case of combined tension and distraction devices placed between pedicle screws, the current invention directly stabilizes the very tissue that is causing the discogenic pain, the annulus, rather than attempting to stabilize the annulus by an external, cantilevered system that has all of the risks and disadvantages of using polyester tension bands and pedicle screws.

The current invention is a basic departure from the prior art at a very fundamental level. The core element of the invention is the simple but broad concept of applying a tension-resisting circumferential band at or near the mid or outer circumference of the annulus. A careful review of the patent and medical literature and prior art did not provide an instance of this fundamental concept having been previously described. Once conceived, the core idea of using a circumferential tension band to reinforce an injured disc annulus led to a number of alternative embodiments, spanning the treatment options all the way from simple reinforcement, to containment of graft material for interbody fusion, to radial containment of a centrally placed compressible or incompressible nuclear replacement material. In other words, the basic concept of the current invention could provide the critical element that would allow a developer and/or a surgeon a new means to structure a new and potentially better annular support for a less invasive early to mid-stage degenerative disc disease treatment method. The invention would also provide an improved means of graft support for a less invasive interbody fusion method. Finally, the invention would provide an improved means of support for nuclear material (biological or non-biological, bioactive or inert, hydrophilic or non-hydrophilic, granular or amorphous)—for nuclear replacement or so-called artificial disc replacement.

The entire content of each and all patents, patent applications, articles and additional references, mentioned herein, are respectively incorporated herein by reference.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. § 1.56(a) exists.

BRIEF SUMMARY OF THE INVENTION

The invention provides for an expandable tubular member or band which has side walls and may include a fill opening. However, the expandable band does not require either a bottom or a top as it has been found that a suitable enclosure is created by placing such a band within a reamed out intervertebral space. Pressure within the interior of the band is exerted primarily against the side walls and the adjacent vertebrae surfaces. The pressure exerted by the bone graft material at the top and bottom is exerted against the exposed bone of the adjacent vertebrae which encourages bone growth through the band interior. The bone graft material is contained within the tube by a combination of the natural bony top and bottom together with the sidewall of the band.

The current invention provides a novel means to support the diseased and/or weakened annulus of the disc. This support would offer improved resistance to stresses placed on the spine and therefore would reasonably result in decreased pain and improved function to any individual suffering from the degenerated disc disease condition.

In addition to simply reinforcing the diseased annulus of the disc, the devices based on the invention herein described could also provide a means to retain and contain materials that might be inserted or injected into the disc in an attempt to heal the annulus, to replace the natural nucleus, or to create a bony fusion between the two adjacent vertebral bodies.

In at least one embodiment of the invention, the invention provides a flexible implant that may be inserted into a cavity formed in a degenerating disc. The flexibility of the band allows it to be inserted through a relatively small opening in a disc or vertebral space. The band is then positioned so its fill opening, if any, may receive biological fill material. This material is packed into the interior flexible band, causing the band to expand and conform to the cavity formed in the disc or vertebrae. Fill material is added until enough material is present to expand the disc to the desired position. At this time, the band fill opening is closed to prevent egress of the fill material.

In at least one embodiment of the invention, the invention provides for a pliable band or hoop that is flexible to normal handling, but cannot stretch circumferentially once it has reached the limits of its circumferential length. The band may have a structural portal to be used for filling, or it may simply be constructed of a fabric-like material that allows a fill tube to perforate its walls to allow for filling. In the latter case, the perforated wall tends to self-seal once the fill tube is withdrawn. The band may be flat or tubular in cross-section. However, unlike a balloon, the band does not require either a bottom or a top, as we found that a top and bottom are unnecessary when using a band or hoop to enclose material injected into a reamed out intervertebral space.

As long as the width of the band is approximately equal to the annulus height (or stated another way, the distance from one vertebral peripheral end-plate to its neighbor) the band serves well to contain particulate material inserted into the center of the disc cavity, without the need for a complete spherical enclosure, as would be provided by a balloon. Since in the case of the reamed out interdiscal cavity, the top opening and bottom opening of the band would be covered by dense vertebral bone, it is not necessary to enclose inserted particulate graft or other material in these regions.

Pressure within the cavity, as would occur when a surgeon injects material into its central region interior to the band, is exerted radially against the band and the adjacent vertebral surfaces. As the internal cavity is filled with incompressible material, such as bone graft or bioceramic beads or granules, radial displacement beyond the circumference of the band is restricted. Therefore, any additional injected material would be directed north and south against the vertebral bodies. This action would increase the distance between the vertebral bodies, and produce a so-called disc distraction. This distraction is known to have three salutary results. First, it stabilizes the motion segment by tightening the ligamentous structures. Second, it opens the exiting holes for spinal nerves -the so-called neural foramina- and thus relieves certain types of nerve compression disorders. Third, this improved stability is necessary to allow for bony ingrowth and through-growth, to produce an interbody fusion. The pressure exerted by the bone graft material at the top and bottom is directed against the exposed bone of the adjacent vertebra. This produces an intimate contact that encourages bone growth through the interior of the cavity.

In at least one embodiment, the invention consists of any continuous band or ring that would be placed around and near the outer margin of the intervertebral disc. A suture or preferably a flattened, braided or woven strand or cord, for instance, that was placed circumferentially about a disc and tied to make a tension-resisting ring, would qualify. Modern endoscopic surgical tools, combined with sophisticated surgical navigation systems make this option more practical and safer than would have been possible a few years ago.

In yet another embodiment, the band would be preformed to match the anatomy of the patient. It would also be available in a variety of circumferences, plies, thicknesses, widths (in the superior-inferior dimensions), weave patterns, materials and filament diameters. The band would be flexible enough to fit through a small hole made in the annulus, such as during a routine disc hernia removal operation. After removal of the disc hernia, the surgeon would introduce an expandable reamer and thereby remove the degenerated nucleus, the cartilage end plate, and the inner annulus, leaving the outer annulus intact. Examples of such a procedure and expandable reamers are described in U.S. Pat. No. 5,445,639 to Kuslich et al. and co-pending U.S. Pat. App. No. 60/182,610 to Kuslich et al., filed Feb. 15, 2000, the entire contents of both being incorporated herein by reference.

The properly sized band would be pushed through the disc portal, whereupon, owing to its inherent springiness, or as a result of material being injected in the interior of the disc, the hoop or band would expand radially against the outer annulus. Perforating the mesh fabric of the band, by means of a pointed fill tube, would allow the surgeon to fill the cavity with significant pressure using graft material; perhaps by the use of a graft injection system such as described in a co-pending U.S. patent application Ser. No. 09/738,726 filed Dec. 15, 2000 and entitled Tool to Direct Bone Replacement Material, to Kuslich et al., and is a continuation in part application of U.S. pat. app. Ser. No. 09/608,079 the entire contents of both being incorporated herein by reference. The resulting compressed graft, held from further expansion by the vertebral bone above and below, and the band or hoop radially, would change phase from liquid-like to solid-like, as is known to occur when granular materials are subjected to compression loading (See: *Friction in Granular Flows*, by H. M. Jaeger, Chu-heng Liu, S. R. Nagel and T. A. Witten, Europhysics Lett. 11, 619 (1990); *Granular Solids, Liquids, and Gases,* by H. M. Jaeger, S. R. Nagel and R. P. Behringer, Rev. Mod. Phys. 68, 1259 (1996); and *IUTAM Symposium on Segregation in Granular Flows (Solid Mechanics and its Applications)*, Vol. 81, October 2000). This phase change has been observed and scientifically characterized by our laboratory experiments and by the work described in U.S. Pat. No. 5,331,975 to Bonutti (see also *Formation of Structural Grafts From Cancellous Bone Fragment,* by P. M. Bonutti, M. J. Cremens, and B. J. Miller, Am. J. Ortop. Jul. 27, 1998: 499–502); each of the above references being incorporated in their entirety herein by reference. This phase change would result in a construct that is capable of both stabilizing the motion segment in the short run, and would foster the development of a solid bony fusion over the long run.

To state the process in another way: the invention provides a pliable implant that may be inserted into a cavity formed in a degenerating disc. The flexibility of the band allows it to be inserted through a relatively small opening in a disc or vertebral space. The band is then positioned so its fill opening may receive fill material. This material is packed into the region interior to the band, causing the band to expand and conform to the cavity formed in the disc or vertebrae. Fill material is added until enough material is present to expand the disc to the desired position. At this time, the band fill opening is closed, or allowed to self-seal to prevent egress of the fill material.

All U.S. patents and applications and all other published documents mentioned anywhere in this application are incorporated herein by reference in their entirety.

The invention in various of its embodiment is summarized below. Additional details of the invention and/or additional embodiments of the invention may be found in the Detailed Description of the Invention below.

The abstract provided herewith is intended to comply with 37 CFR 1.72 and is not intended be used in determining the scope of the claimed invention.

BRIEF DESCRIPTION OF THE DRAWINGS

A detailed description of the invention is hereafter described with specific reference being made to the following drawings.

DETAILED DESCRIPTION OF THE INVENTION

This invention may be characterized as an improvement of the inventor's inventions described in U.S. Pat. Nos. 5,571,189 and 5,549,679, the disclosures of which are incorporated herein by reference.

Figure 1:
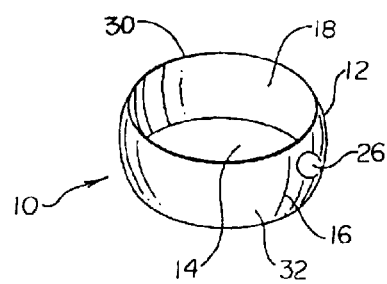
FIG. 1 is a perspective view of a first embodiment of the invention;.
Figure 2:
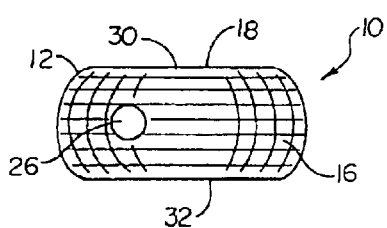
FIG. 2 is a side view of the embodiment of FIG. 1.
Figure 3:
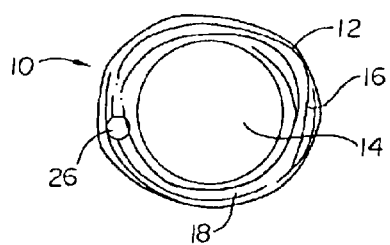
FIG. 3 is a top view of the embodiment of FIG. 1.
Figure 4:
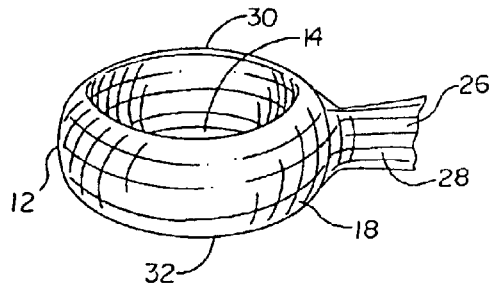
FIG. 4 is a perspective view of an embodiment of the invention having an elongate fill opening.

With reference to the Figures, FIGS. 1–3 illustrates an embodiment of the inventive implant 10 which consists of a sidewall band 12, which may be characterized as being substantially tubular or ring like in shape. Preferably the band 12 is circular, however other elliptical shapes and other geometric shapes may also be used.

The band 12 is pliable and malleable before its interior space 14 (not shown in FIG. 2) is filled with the contents to be described. While in this initial condition, the band 12 may be passed, in a collapsed state, through a relatively small tube or portal, such as recited in U.S. Pat. Nos. 5,571,189 and 5,549,679, the entire contents of both references being incorporated herein by reference. This feature is important because access to the intervertebral disc is limited by anatomy and therefore safety considerations direct us to use the smallest possible portal of entry.

Figure 6:
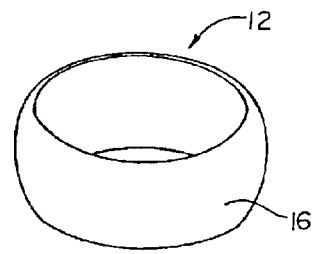
FIG. 6 is a perspective view of an embodiment of the invention wherein the band is a molded material.

The band 12 may be constructed in a variety of ways. The band material 16 may be etched, woven or braided material such as a weave of NITINOL fibers, or a form-molded material such as shown in FIG. 6. The material or fabric 16 may be fluid impermeable or may be provided with a density that will allow ingress and egress of fluids and solutions and will allow the ingrowth and through-growth of blood vessels and fibrous tissue and bony trabeculae. Where the material 16 is provided with such a porous construction, pores or weave gaps are preferably tight enough to retain small particles of enclosed fill material, such as ground up bone graft, other tissues or solid pieces of bone inducing material such as hydroxyapatite or other biocompatible materials known to promote bone formation.

Where the material 16 of the band 12 is porous, such as in the embodiment shown in FIGS. 1–4, the pores or openings 18 of the fabric will have a diameter of about 0.25 mm to about 5.0 mm. The size is selected to allow tissue ingrowth while containing the material packed into the bag.

Figure 7:
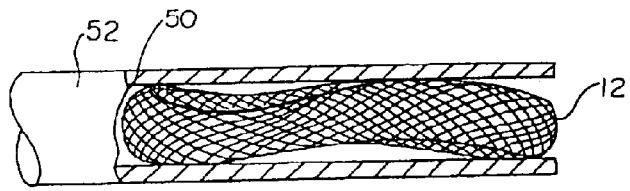
FIG. 7 is a side view of an embodiment of the invention shown in the reduced state within a storage/delivery tool.
Figure 8:
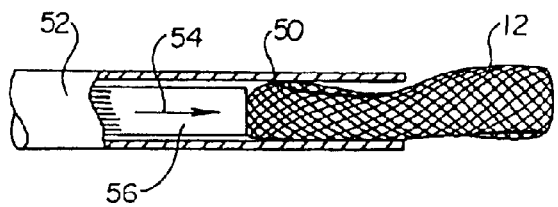
FIG. 8 is a side view of the embodiment shown in FIG. 7 wherein the inventive band is being removed from the storage/delivery tool.
Figure 9:
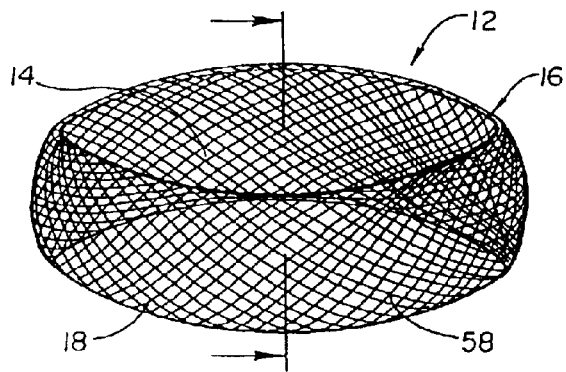
FIG. 9 is a perspective view of an embodiment of the invention wherein the inventive band has a woven, double walled configuration.

The material 16 of the invention must be flexible enough to allow it to be collapsed and inserted into an opening smaller than the expanded band size. As may be seen in FIGS. 7 and 8, the band 12 is sufficiently flexible so that it may be positioned into a holding chamber 50 of a storage tube or delivery device 52. Depending on the exact construction of the band 12, the band may be compacted into a substantially smaller configuration than the band is capable of attaining when packed with graft material. The delivery device however, is sized such that the device 52 may be inserted into a surgical opening wherein the band 12 is drawn or pushed by plunger 56 out of the chamber 50, as indicated by the direction of the arrow 54 as shown in FIG. 8. The band 12 may be used to repair and/or replace a vertebral disc 23 as may be seen in FIG. 5 wherein the band is placed between adjacent vertebral bodies 24. The band 12 may be inserted into a small opening in the annulus 21 of the disc 23 and filled from within the disc. Alternatively, the band 12 may be inserted within a hollowed region of a vertebra 24 to provide support thereto, or may be utilized to replace an entire vertebral body 24. In order to ensure that the supportive quality of the band 12 is maintained, the fill material used in conjunction with the band 12 is preferably minimally elastic if at all.

Accordingly, the fabric band 12 may be formed from a polymeric material to which a plurality of perforations are formed or added. It need not be woven and may be molded, such as the embodiment shown in FIG. 6, or otherwise formed as is well known in the art. The preferred material may provide the ability to tailor bioabsorbance rates. Any suture-type material used medically may be used to form the band 12. The band 12 may be formed of plastic or even metal. The band 12 could be formed from a solid material. The band 12 may be partially or totally absorbable, metal, plastic, woven, solid, film or an extruded balloon.

Figure 23:
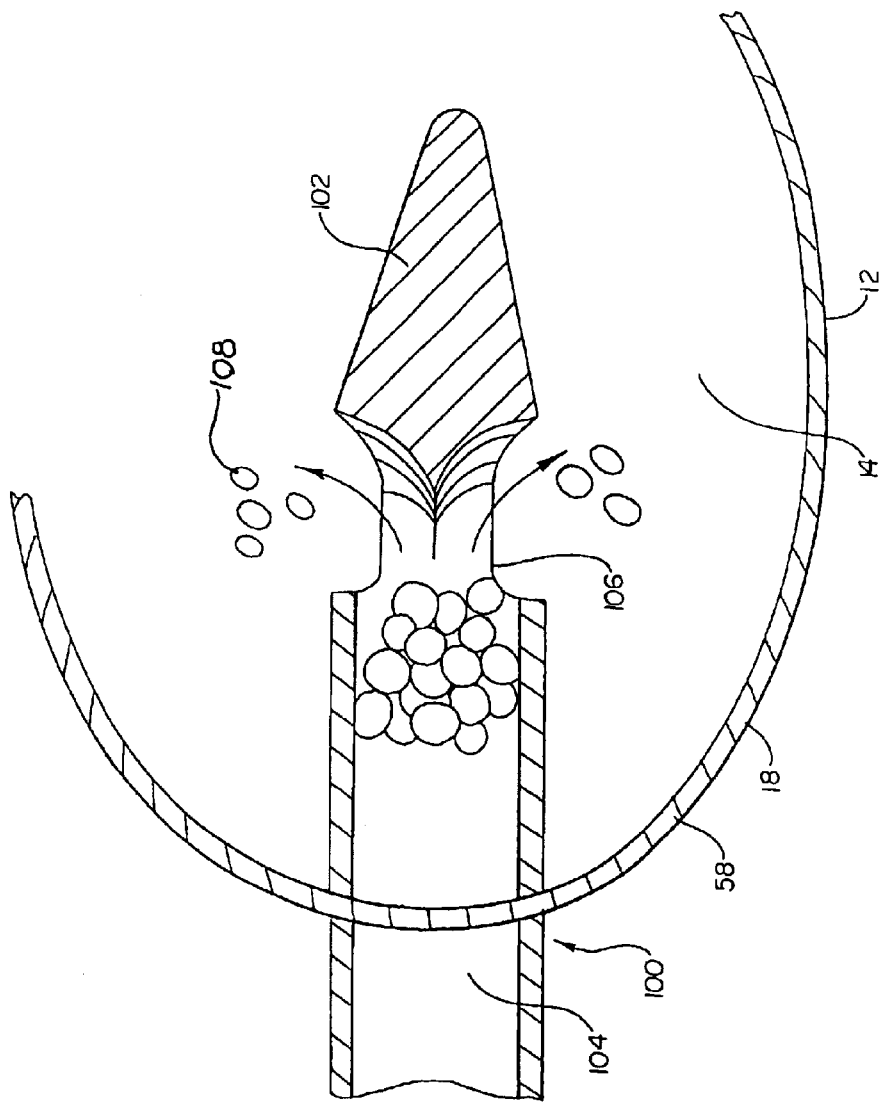
FIG. 23 is a top down cut away view of a tool similar to the tool of FIG. 19 as may be seen during graft insertion.

Preferably the material 16 is light, biocompatible, flexible and easily handled, but is also very strong in terms of resisting tension, and thus unlikely to rip or tear during insertion and expansion. When the device is expanded through insertion of fill material, such as is depicted in FIG. 23, the band 12 expands to a predetermined shape, and in doing so, it fills a previously excavated space 20 between the vertebral bodies and/or within a vertebral body, such as may be seen in FIG. 5. This filling results in the separation of the vertebral bodies 24 and results in the stabilization of the spinal motion segment, indicated generally at 22.

As may be seen in FIGS. 1–2, and 4–5, the band 12 may be characterized as having two ends 30 and 32. One or both ends 30 and 32 may be open as defined by the band 12. As may be seen in FIG. 5, where the band 12 is utilized to replace a disc, the openings 30 and 32 are characterized as being less than the diameter of the surrounding vertebral bone, thus assuring containment of the graft material within the confines of the interior 14 of the band 12. Where only a single end 30 or 32 is open, the material 16 which covers one or more of the openings is porous to allow for bone growth therethrough such as has been described above.

In addition, as may be seen in FIGS. 1–2 and 4–5, the band 12 may be equipped with a fill opening 26. The fill opening 26 must be large enough to accommodate passage of fill material as well as the means of placing fill material into the interior space 14 of the band 12. A device which may be suitable for passing through the fill opening 26 for insertion of fill material is described in co-pending U.S. pat. app. Ser. No. 09/608,079 as discussed above.

Preferably the opening 26 includes a means of preventing passage of fill material out of the interior space 14. In the embodiment shown in FIG. 4, the opening 26 includes an elongate passage 28 which may be tied off or otherwise sealed subsequent to insertion of the fill material.

Figure 5:
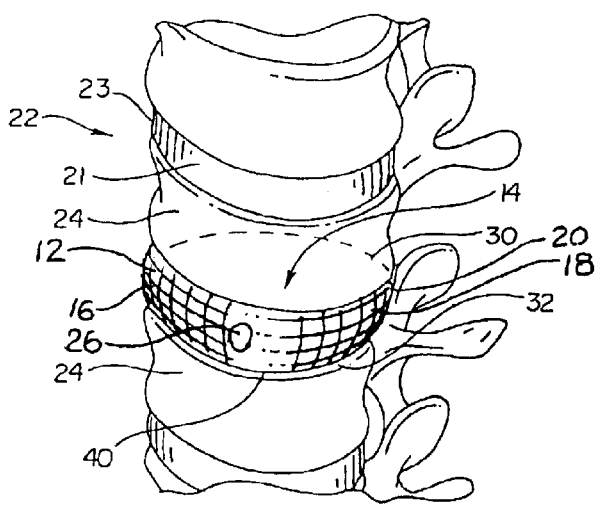
FIG. 5 is a perspective view of an embodiment of the invention as it may appear when used to replace a spinal disc.

As may be further seen in FIG. 5 when the band 12 is inserted between two vertebra 24 or within a disc 23 or other hollowed region of an intervertebral space and filled with fill material, the fill material will push against the vertebral surfaces 40 which are adjacent to the top 30 and bottom 32 of the band 12. The band 12 in combination with the vertebral surfaces 40 will contain the fill material within the interior space 14.

In the embodiment of the invention wherein the band material 16 is woven from one or more fibers, the fibers may be composed of a variety of materials as previously discussed. In the various embodiments shown in FIGS. 9–18, the band 12 may be constructed from one or more metal fibers such as, for example, NITINOL fibers 58, which have been woven or braided together into the desired band shape. The use of a shape-memory material such as NITINOL, or a material such as steel, titanium or other metal, provides the band with sufficient mechanical strength to resist stretching or expansion as a result of the build up of graft material in the interior 14. In addition, such shape-memory materials allow the band to be collapsed prior to insertion, such as may be seen in FIGS. 7 an 8 yet which will tend to reacquire its original shape once implanted.

Figure 10:
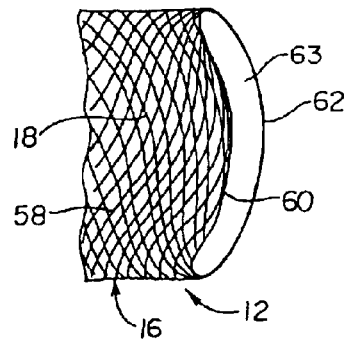
FIG. 10 is a perspective cut away view of the embodiment shown in FIG 9.
Figure 11:
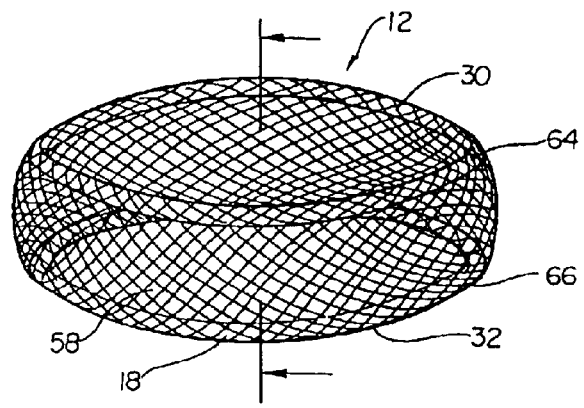
FIG. 11 is a perspective view of the embodiment of the invention shown in FIG. 9 wherein the inventive band further includes latitudinally oriented support bands.
Figure 12:
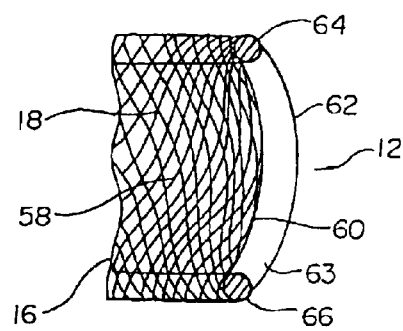
FIG. 12 is a perspective cut away view of the embodiment shown in FIG. 11.

FIGS. 9–18 depict a wide variety of band configurations. As may be seen in FIGS. 9–14 the band 12 may be characterized as a double walled band or a loop of material folded back upon itself. Such a double walled configuration may be seen as having a inner wall 60 which is continuous with the outer wall 62 and defining a toroid shaped space 63 therebetween as seen in FIGS. 10 and 12.

Figure 14:
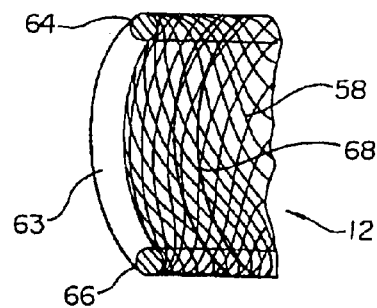
FIG. 14 is a perspective cut away view of the embodiment shown in FIG. 13.

As seen in FIGS. 12 and 14, the toroidal shaped space 63 may be filled, in whole or in part with pharmaceuticals for drug delivery to the implantation site. The toroid space 63 may also be filled, subsequent to implantation into a vertebral body with a biocompatible cement or other material for providing the band 12 with additional support.

The double walled construction may provide the band 12 with increased strength to provide additional mechanical support for the graft material contained in the interior 14. In addition, the double walled construction may be configured to allow the various openings 18 of the respective walls 60 and 62 to partially overlap. As a result, the fibers 58 of one wall, for example inner wall 60, may overlap the openings 18 of the other wall, for example outer wall 62, thereby effectively reducing the size of the openings 18. As a result, a band 12 having a double walled construction may not require any more fibers 58 than a single walled band such as may be seen in FIGS. 15–18. However, it may be desirable to provide a double walled band 12 with a denser weave of fibers 58 for the purpose of providing the band 12 with greater mechanical strength.

Turning to FIGS. 11 and 12, a double walled band 12 may also include one or more latitudinally disposed support members such as members 64 and 66 shown. The individual support members 64 and 66 may be positioned in any manner around the circumference of the band 12. In the embodiment shown, the members 64 and 66 are respectively disposed the first or top opening 30 and the second or bottom opening 32. In addition the members 64 and 66 are located between the inner wall 60 and outer wall 62. The members 64 and 66 may be used to support the material 16 of the band by weaving the fibers 58 about the members 64 and 66, such as may best be seen in FIG. 12.

The members 64 and 66 may be constructed from the same or different material as fibers 58. In addition, the members 64 and 66 may be one or more wires or fibers woven or braided together and oriented in the latitudinal orientation shown. Alternatively, one or more fibers may be equatorially oriented, or may be otherwise positioned anywhere around the circumference of the band 12.

Figure 13:
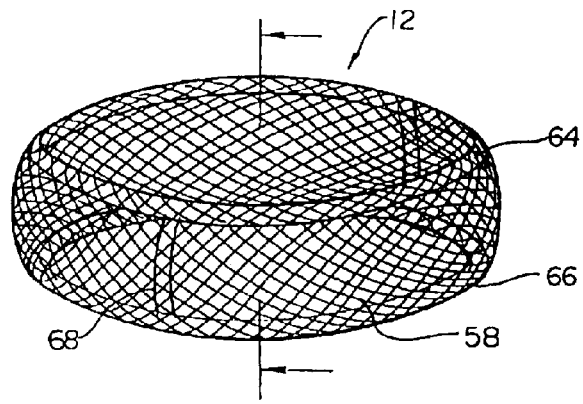
FIG. 13 is a perspective view of the embodiment of the invention shown in FIG. 11 wherein the inventive band further includes longitudinally oriented support bands.

In addition to providing the band 12 with one or more latitudinally oriented wires or members 64 and 66, the band may also include one or more longitudinally oriented members 68 such as may be seen in the embodiment shown in FIGS. 13 and 14. In the embodiment shown, the longitudinal members 68 vertically cross the band 12 to join the latitudinal members 64 and 66. In addition, the longitudinal members 68 are oriented substantially perpendicular to the latitudinal members 64 and 66. The longitudinal members 68 provide the band with compression support relative to the surrounding vertebra. The members 68 may be woven into the fibers 58 or may be independent of the band's woven configuration. In one embodiment where the band is equipped with longitudinal members 68 as well as latitudinal members 64 and 66, the various members may act as a frame work which supports the woven fibers 58 of the band 12.

As with the latitudinal members 64 and 66, the longitudinal members 68 may be constructed out of any suitable material. Such material may be different from or the same as the fibers 58. Additionally, the members 68 may be characterized as one or more fibers 58 oriented in the longitudinal direction shown.

Figure 15:
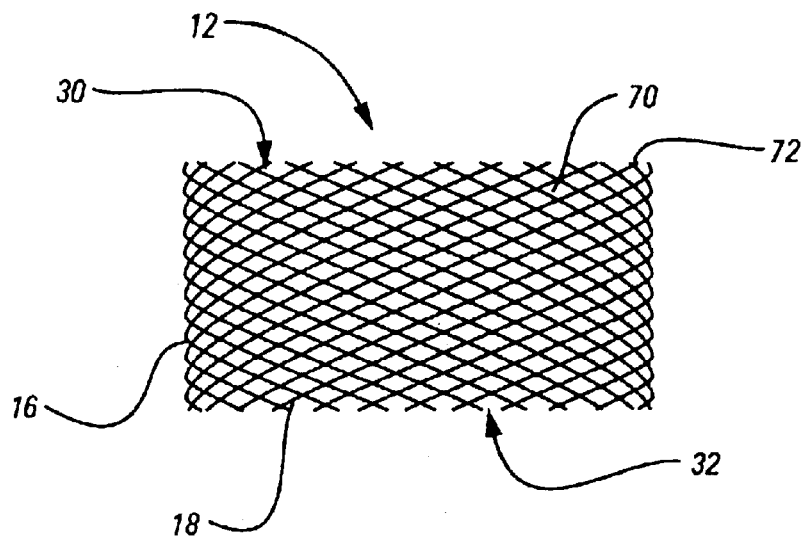
FIG. 15 is a side view of an embodiment of the invention wherein the inventive band has a single walled configuration.

In the various embodiments shown in FIGS. 15–18 it may be seen that the band 12, may be provided with only a single wall construction as opposed to the double walled construction previously described. As shown in FIG. 15, because the single wall 70 is not a continuous overlapping loop of material such as may be seen in FIGS. 9 and 10, the single walled band 12 shown in FIG. 15 may have openings 30 and 32 which have fairly jagged or non-uniform edges 72. While the material 16 of the band 12 may not necessarily be of sufficient hardness to penetrate the surrounding vertebral bone, the non-uniform nature of the edges 72 of the band 12, provides band 12 with surfaces which may tend to more readily engage the surfaces of the surrounding vertebral bone, thereby preventing the band 12 from shifting or otherwise moving during the graft injection process or thereafter.

Figure 16:
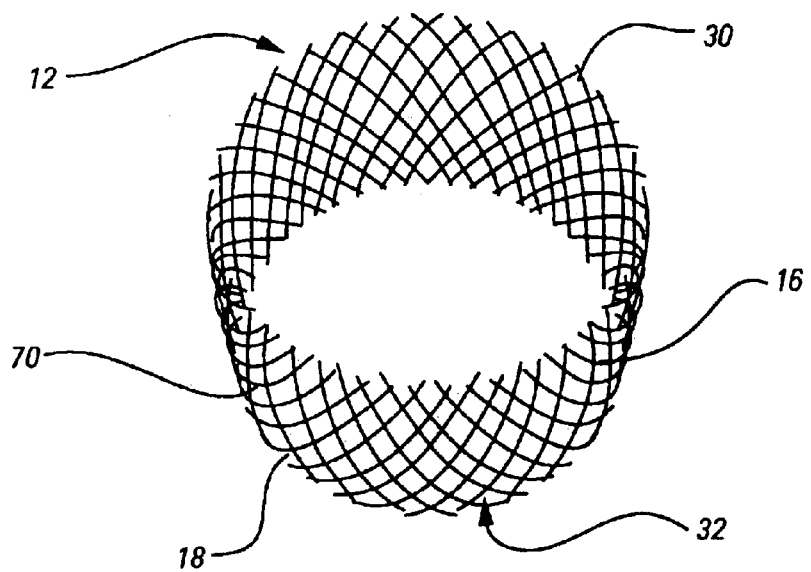
FIG. 16 is a perspective view of an embodiment of the invention.
Figure 17:
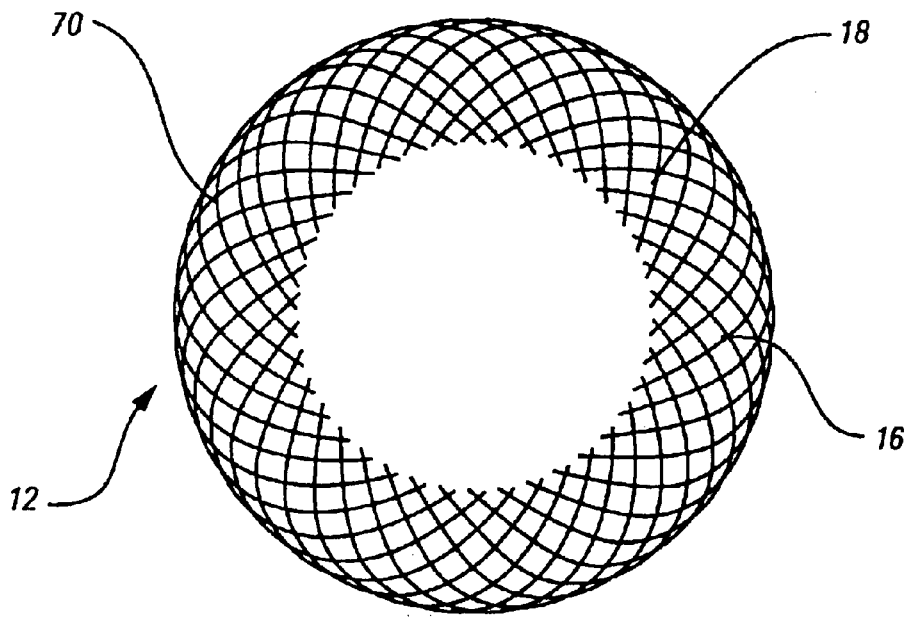
FIG. 17 is a top down view of an embodiment of the invention.
Figure 18:
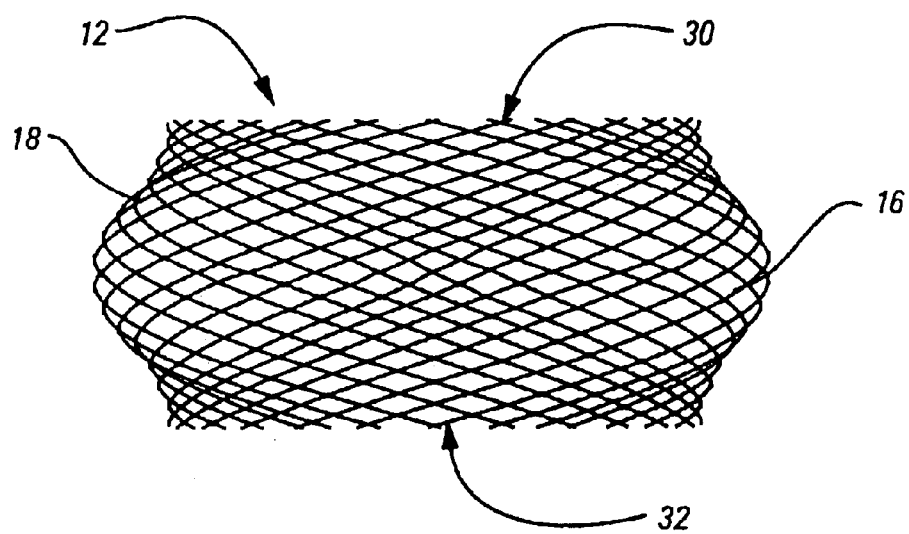
FIG. 18 is a side view of the embodiment of the invention shown in FIG. 15 wherein the inventive band is shown is a partially reduced state.

As shown in FIGS. 15 and 16 the single walled band 12 may be configured to have an essentially cylindrical shape. The cylindrical shape may be compressed into an elongated band such as may be seen in FIGS. 7 an 8 prior to insertion into the body. However, the band 12 may be configured to include other shapes, notably the rounded configuration shown in FIG. 17, after the band 12 is inserted into a vertebral body. As may be seen in FIG. 18, the malleability of a single walled band is illustrated. As with all embodiments of the present invention, the band 12 may be significantly distorted, collapsed or otherwise manipulated in order to collapse the band into a reduced configuration such as may be seen in FIGS. 7 and 8. The present invention may be distorted in either or both the radial and longitudinal directions while retaining its ability to expand subsequent to insertion into the spinal area.

Figure 21:
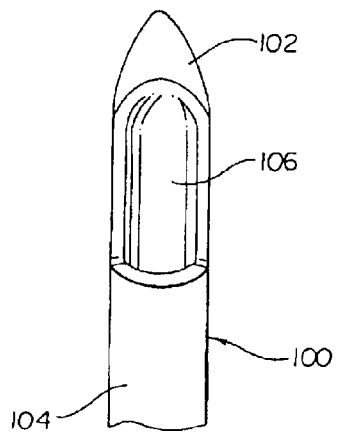
FIG. 21 is a top down view of the tool of FIG. 19.
Figure 22:
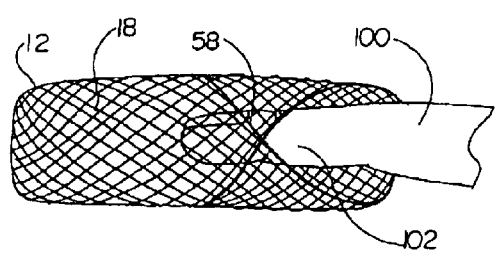
FIG. 22 is a side view of the tool of FIG. 19 seen dislocating the fibers of an embodiment of the inventive band.

As shown in FIG. 22 and 23, the band 12 is shown with a fill insertion tool 100 being inserted into the interior 14 of the band 12 by passing through one of the spaces or pores 18. The shape of the tool 100 as may best be seen in FIGS. 19–21 is essentially an elongate shaft 104 having a tapered or pointed distal end 102.

Figure 19:
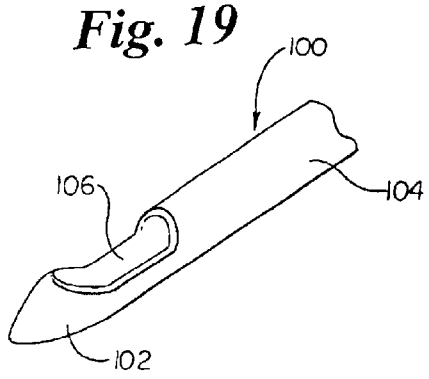
FIG. 19 is a perspective view of a graft insertion tool suitable for use with the inventive band.
Figure 20:
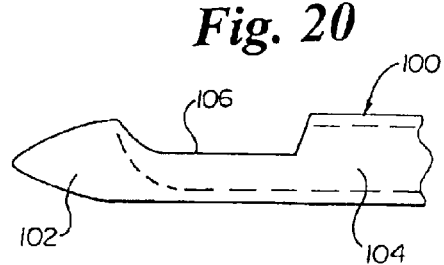
FIG. 20 is a side view of the tool shown in FIG. 19.

As is shown in FIGS. 19–21, an example of a fill insertion tool which is suitable for use in the various embodiments of the invention is illustrated. The tool 100 is further disclosed in a co-pending U.S. patent application Ser. No. 09/738,726 filed Dec. 15, 2000 and entitled Tool to Direct Bone Replacement Material, to Kuslich et al., and is a continuation in part application of U.S. pat. app. Ser. No. 09/608,079 the entire contents of both being incorporated herein by reference.

The tapered distal end 102 of the tool 100 is sized to enlarge the opening 18 to allow passage of the tool 100 into the interior 14 by pushing aside the various fibers 58 as may best be seen in FIG. 22. The fibers 58 are disposed to open the pore 18 from its nominal diameter of about 0.25 mm to about 5 mm to an enlarged opening sufficient to allow passage of a portion of the shaft 104 therethrough.

The extent of tool penetration into the band interior 14 must be sufficient to allow the side opening 106 to be fully contained within the band interior 14. The tool 100 may include more than 1 side opening 106.

As shown in FIG. 23, the side opening 106 allows insertion of the bone graft or other types of fill material 108 into the band interior 12. The tool 100 may include a piston plunger or other means (not shown) for pushing fill material 108 from within the shaft 104, through the side opening 106 and into the band interior 14.

If the internal diameter of the shaft 104 may be about 1.5 mm to 5 mm and is preferably approximately 2.5 mm in diameter. The length of the side opening 106 is preferably between about 1 ½ to 3 times the internal diameter of the shaft 104.

The distal end 102 of the tool 100 is preferably angled to direct the flow and to break down any material that has packed back into more discrete pieces.

Figure 24:
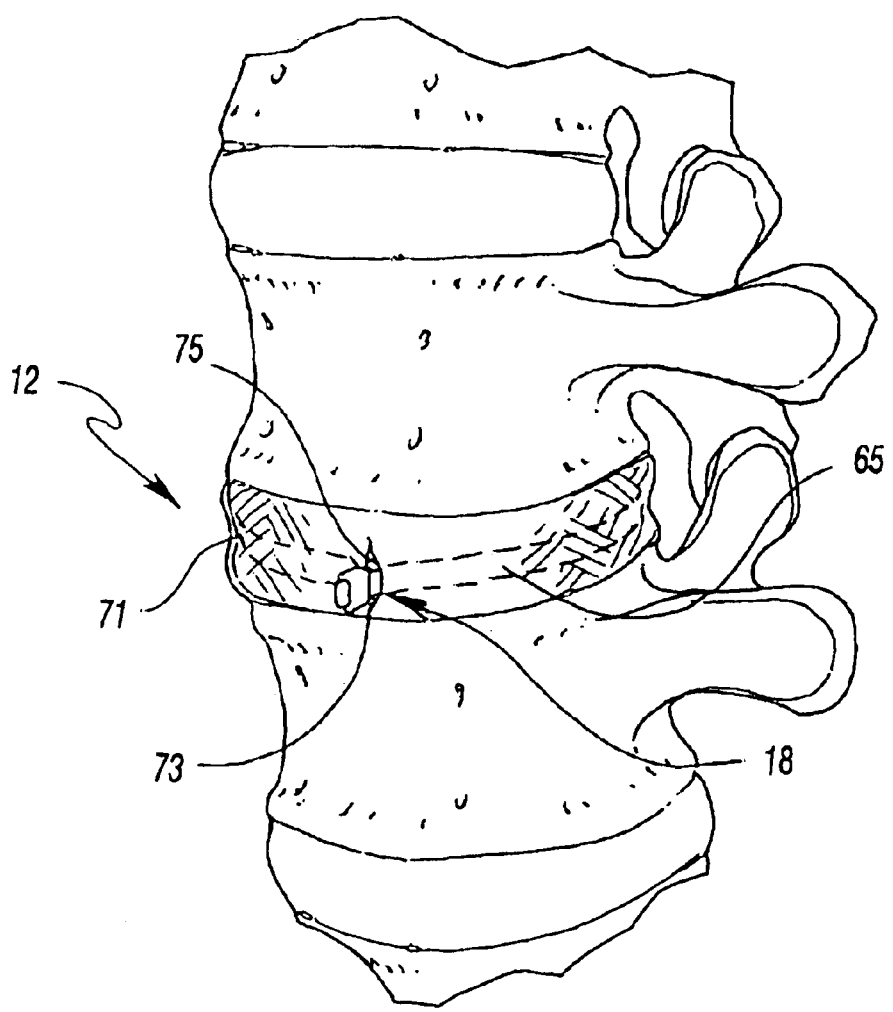
FIG. 24 is a perspective view of a portion of a spine wherein an embodiment of the invention is shown in place.

Turning to FIG. 24 an embodiment of the band 12 is shown, wherein the band 12 includes at least one circumferentially disposed tightening or cinching member 65 shown. The cinching member 65 may be positioned in any manner around the circumference of the band 12 as previously described. In the embodiment shown, each member 65 extends about the mid-portion 71 of the band 12 and includes ends 73 and 75 that extend outward from one of the pores 18 where they may be pulled together and secured or tied to one another in the manner shown. When the band 12 is properly filled with fill material in any of the manners previously mentioned, the ends 73 and 75 may be cinched together in order to constrict the mid-portion of the band 12 so that the band 12 takes on a concave shape, such as is shown. The concave shape may provide greater support and flexibility to the surrounding spinal bodies and to the spine itself. When ends 73 and 75 are pulled together and secured, not only is the band provided with a concave shape, but any fill material positioned therein is pushed together for more effective engagement with surrounding tissue as well as with itself and the band 12.

Figure 25:
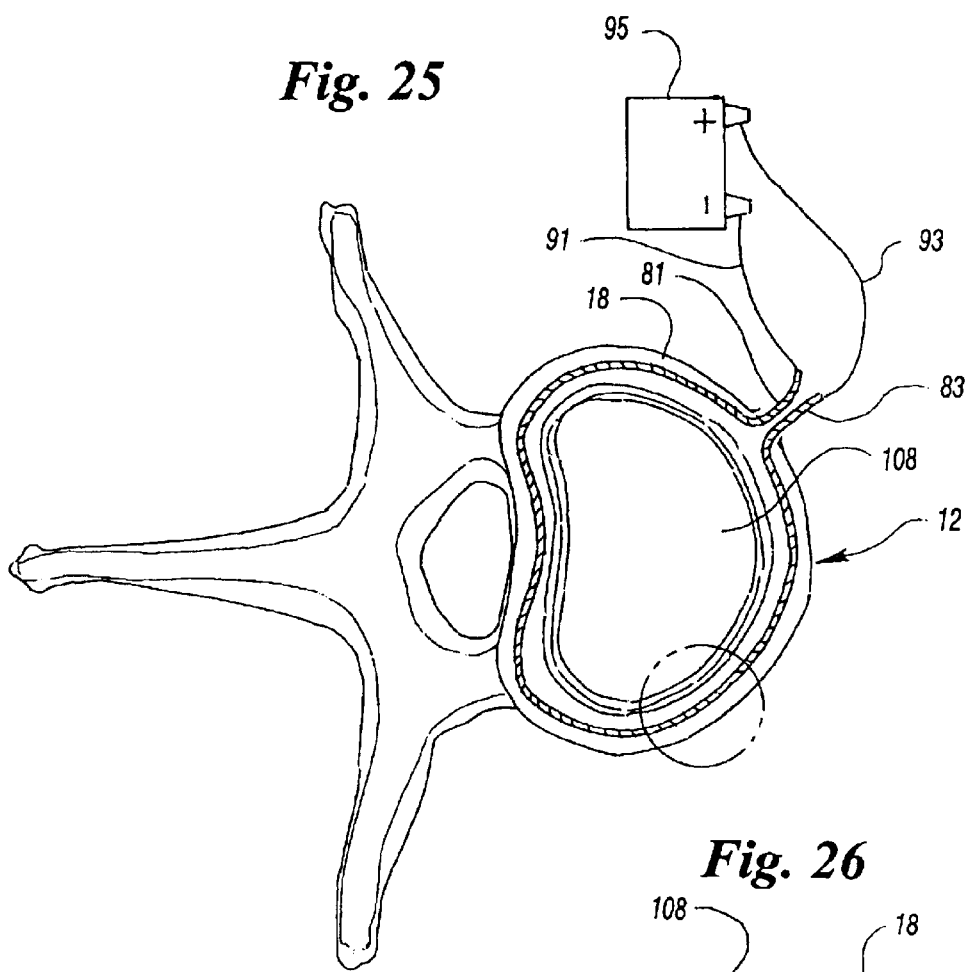
FIG. 25 is a cross-sectional view of a spinal body which includes an embodiments of the invention therein.

In the various embodiments described herein, it may be desirable to stimulate growth of bone through the band 12 or fill material 108 contained therein, by direct or indirect application of electrical current. In the various embodiments described herein, the band 12 may include portions 81 and 83, where electrical leads 91 and 93 may be readily attached, such as are shown in FIG. 25. Leads 91 and 93 are in electrical communication with an electrical power source 95 which provides sufficient current to stimulate bone growth through and adjacent to the band 12. In at least one embodiment, the leads 91 and 93 may be inserted through pores 18, as previously shown and described, to directly stimulate the fill material 108.

Figure 26:
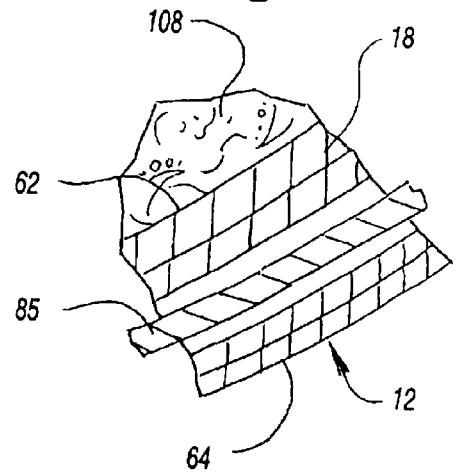
FIG. 26 is a close-up cut away view of a portion of the embodiment shown in FIG. 25.

The portions 81 and 83 may be part of a electrically conductive member 85 which is disposed within the walls 60 and 62 of the band 12, such as is shown in FIG. 26. Alternatively, the entire band 12 is electrically conductive, In yet another embodiment at least a portion of one or both walls 60 and 62 are electrically conductive and/or electrically insulated.

Figure 27:
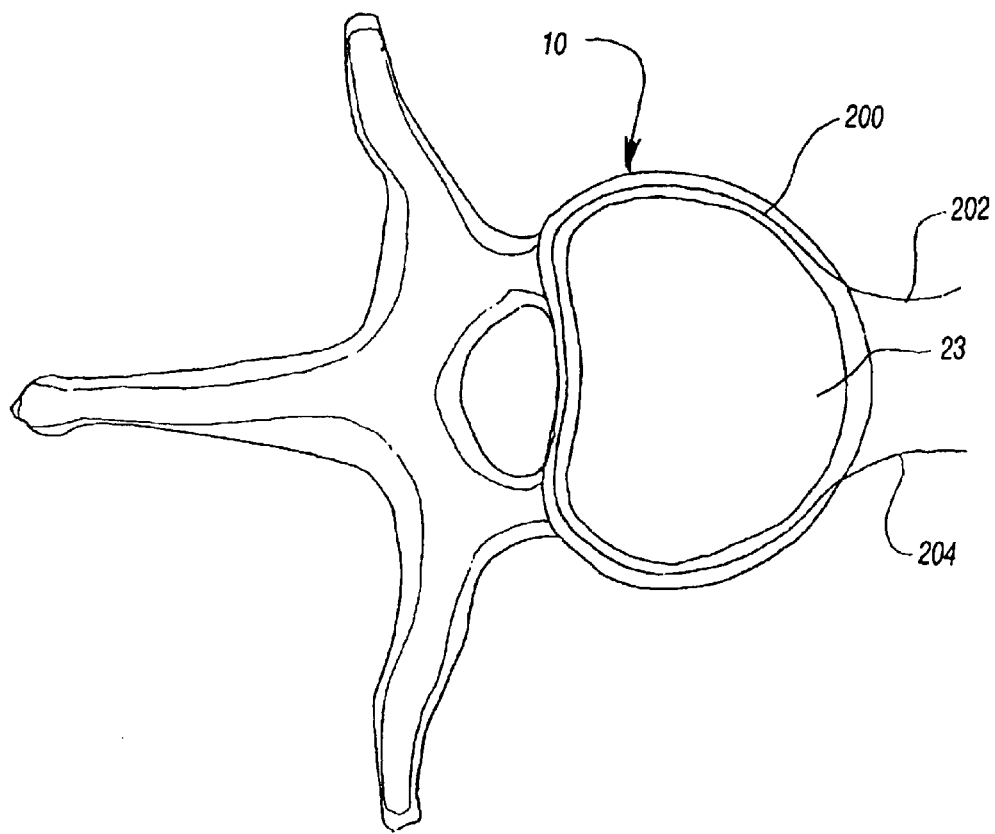
FIG. 27 is a cross sectional view of a spinal segment which includes an embodiments of the invention being positioned thereabout.
Figure 28:
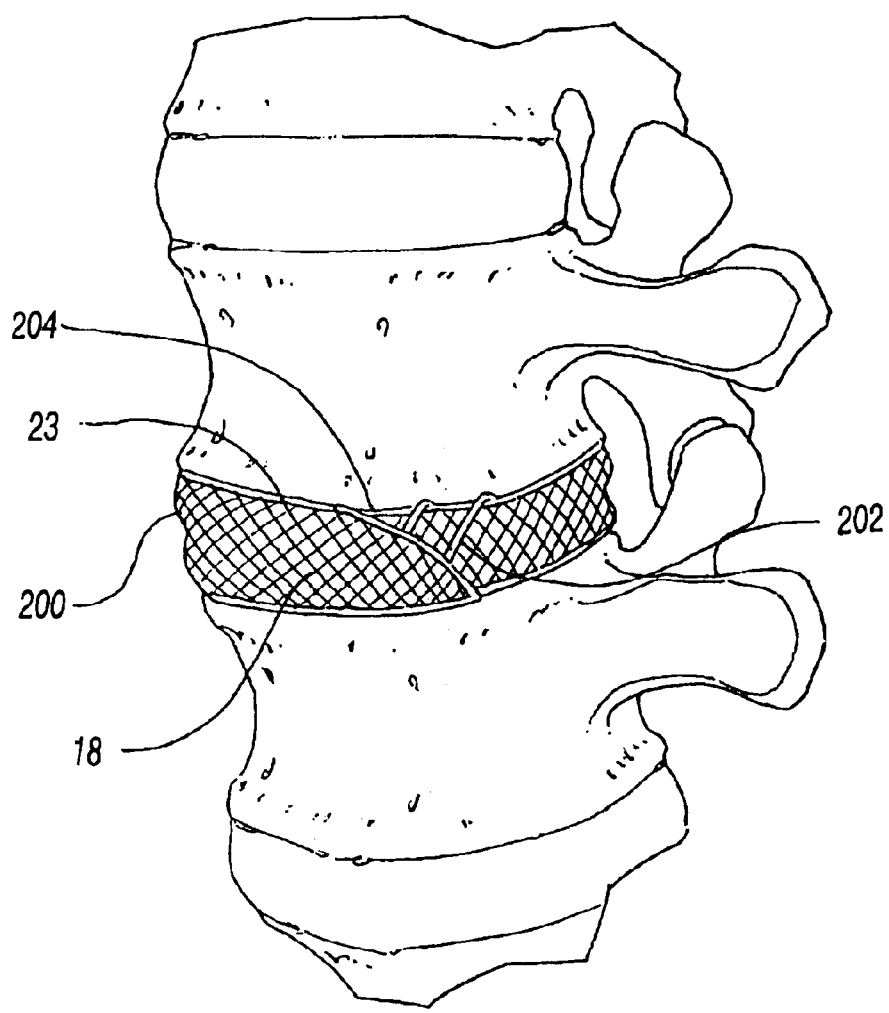
FIG. 28 is a perspective view of the spinal segment shown in FIG. 27, wherein the embodiment of the invention is shown secured thereto.

In an alternative embodiment of the invention shown in FIG. 27 and 28, the implant 10 may be characterized as a linear member or members 200 which is disposed about a vertebral disc 23 in a manner such as is shown in FIG. 27. The member 200 may be a one or more of a combination of strands, threads, fibers, cords or other substantially linear portions of material which include a first end 202 and a second end 204 that are capable of being tied or otherwise secured together. Preferably, the member 200 has a height sufficient to cover the entire exposed surface of the disc 23. Some examples of materials which are suitable for use as member 200 or in its construction include, but are not limited to: Secure Strand available from Smith & Nephew Inc., THE LOOP™, available from Spineology Inc., and Songer Cable from Medtronic Inc.

Figure 29:
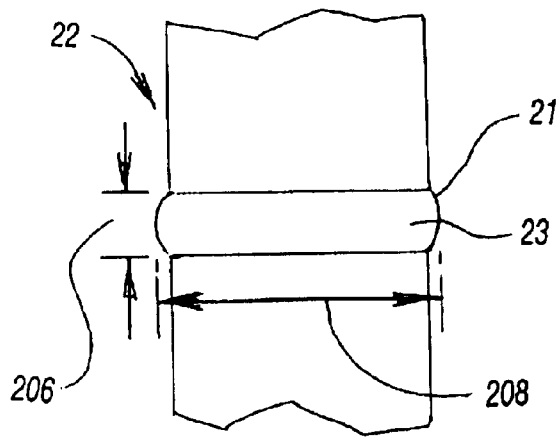
FIG. 29 is a frontal view of a spinal segment shown in cross-section.
Figure 30:
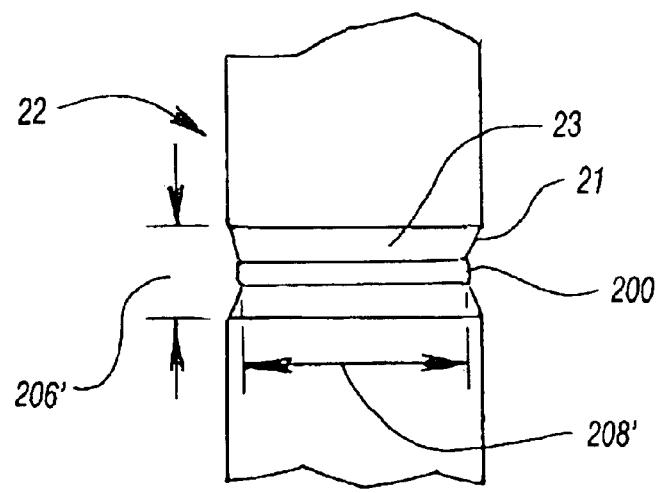
FIG. 30 is a frontal view of a spinal segment shown in cross-section, that includes an embodiment of the invention therewith.

In some embodiments of the invention, one of which is shown in FIG. 28, the member 200 may be constructed of the same material 16 as the previously described embodiments of the invention shown in FIGS. 1–26, and include a plurality of pores or openings 18. Once secured about the disc 23, the member 200 may be further cinched or otherwise tightened about the disc 23 as is shown in FIGS. 29 and 30. By tightening the member 200 about the disc 23, the disc 23 is compressed in order to invaginate the annulus 21 toward its center thereby tightening the annulus fibers. Such tightening will stabilize the spinal motion segment 22 and thereby stiffen that portion of the spine.

In FIG. 29 the annulus 21 of a disk 23 is shown within a spinal motion segment 22 prior to the securement and tightening of member 200 thereabout. It is shown that the annulus 21 of the disk 23 has a predetermined height 206 and a predetermined circumference 208. When the member 200 is disposed and subsequently tightened about the annulus 21, such as is shown in FIG. 30, the circumference is reduced as indicated at reference numeral 208' while the height of the disk is made greater as is indicated at reference numeral 206'.

By securing the ends 202 and 204 of the member 200 about the disc, the member 200 forms a substantially continuous band similar to that previously described. When secured about a disc the member 200 preferably has a substantially concave appearance, relative to the surrounding spinal bodies, such as is shown in FIG. 28. W hen secured about the disc 23, the disc 23 may be further treated with additional therapeutic agents, including fill material via the pores or openings 18, in the manner previously described in relation to the embodiments shown in FIGS. 1–26.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

What is claimed is:

1. A device comprising:
    a generally flexible substantially tabular member sized to fit and expand transversely into a hollowed region of an intervetebral space or intravertebral space;
    the substantially tubular member defining an interior space;
    the interior space extending from a first end of the substantially tubular member to second end of the substantially tubular member;
    at least one end defining an opening;
    the opening in fluid communication with the interior space;
    the substantially tubular member constructed and arranged to expand from a reduced state to an expanded state by the introduction of fill material into the interior space;
    the substantially tubular member including a plurality of pores;
    the plurality of pores being sized to allow ingress and egress of liquids, solutions or small particle suspensions and ingrowth of bony trabeculae or fibrous elements into and through the device when the device is positioned in the hollowed region of a intervertebral space or intravertebral space;
    the plurality of pores being sized to retain the fill material within the interior space of the substantially tubular member;
    the substantially tubular member including at least one fill opening through which the fill material may be introduced into the interior space;
    the at least one fill opening including at least one of the plurality of pores.

2. The device of claim 1 wherein the at least one fill opening is constructed and arranged to prevent egress of the fill material from the interior space.

3. The device of claim 1 wherein the hollowed region of a intravertebral space is defined by a bored out region of a vertebra, the device being inserted into the bored out region of the vertebra.

4. The device of claim 1 wherein the hollowed region of an intervertebral space is defined by a bored out region of a disc, the device being inserted within the bored out region of the disc in the reduced state.

5. The device of claim 1 wherein the first end defines a top opening and the second end defines a bottom opening, the top opening and the bottom opening each being immediately adjacent to surrounding vertebral tissue.

6. The device of claim 1 wherein the substantially tubular member is composed of a polymeric material.

7. The device of claim 1 in combination with a delivery tube, the tube defining a storage chamber, the storage chamber sized to accommodate passage of the substantially tubular member in the reduced state from within the storage chamber into the hollowed region of an intervertebral space or intravertebral space.

8. The device of claim 1 wherein the said fill material is combined with a virus, the virus constructed and arranged to stimulate bone formation.

9. The device of claim 1 wherein said fill material is subjected to electrical energy stimulation.

10. The device of claim 1 said device being subjected to electrical energy stimulation.

11. The device of claim 1 wherein the substantially tubular member further comprises at least one circumferential member, the at least one circumferential member constructed and arranged to constrict a mid-portion of the substantially tubular member when the substantially tubular member is in the expanded state to provide the substantially tubular member with a substantially concave shape.

12. The device of claim 1 wherein the hollowed region of a intervertebral space or intravertebral space is defined by adjacent vertebrae.

13. The device of claim 12 wherein in the expanded state the opening of the at least one end being immediately adjacent to at least one of the adjacent vertebrae.

14. The device of claim 1 wherein the substantially tubular member is composed of a fluid impermeable material.

15. The device of claim 14 wherein the plurality of pores are perforations.

16. The device of claim 1 wherein each of the plurality of pores having a first diameter of about 0.25 mm to about 5 mm.

17. The device of claim 16 wherein the at least one fill opening has a predetermined diameter, the predetermined diameter of the fill opening being larger than the first diameter of any of the plurality of pores.

18. The device of claim 16 in combination with a fill insertion tool, the fill insertion tool constructed and arranged to be inserted into at least one of the plurality of pores, the at least one of the plurality of pores being opened from the first diameter to a second diameter, the second diameter being sized to allow the fill insertion tool to pass into the interior space of the device.

19. The device of claim 1 wherein the substantially tubular member is composed of a woven material, wherein the woven material is comprised of at least one fiber.

20. The device of claim 19 wherein the at least one fiber is constructed at least partially from a shape-memory material.

21. The device of claim 19 wherein the woven material is biocompatible material selected from at least one member of the group consisting of steel, titanium, NITINOL, and any alloys thereof.

22. The device of claim 19 further comprising at least one latitudinally oriented support member.

23. The device of claim 22, the at least one latitudinally oriented support member encircling the opening of the at least one end.

24. The device of claim 19 wherein the substantially tubular member further comprises an inner wall and an outer wall, the inner wall and the outer wall being continuous with one another, the inner wall and the outer wall defining a space therebetween.

25. The device of claim 24 wherein at least one latitudinally oriented member is positioned within the space defined by the inner wall and the outer wall, the at least one latitudinally oriented member supporting the at least one fiber.

26. The device of claim 19 further comprising at least one longitudinally oriented support member.

27. The device of claim 26 wherein the at least one longitudinally oriented support member is constructed of the at least one fiber.

28. The device of claim 26 further comprising at least one latitudinally oriented support member, the at least one latitudinally oriented support member having a perpendicular orientation relative to the longitudinally oriented support member when the device is in the expanded state.

29. A method for stabilizing a spinal motion segment comprising the following steps:

(a) providing a generally flexible substantially tubular member sized to fit and expand transversely into a hollowed region of an intervertebral space or intravertebral space, the substantially tubular member defining an interior space, the interior space extending from a first end of the substantially tubular member to a second end of the substantially tubular member, at least one end defining an opening, the opening in fluid communication with the interior space, the substantially tubular member constructed and arranged to expand from a reduced state to an expanded state by the introduction of fill material into the interior space, the substantially tubular member including at least one fill opening through which the fill material may be introduced into the interior space, the substantially tubular member including a plurality of pores, the plurality of pores being sized to allow ingress and egress of liquids, solutions or small particle suspensions and ingrowth of bony trabeculae or fibrous elements into and through the device when the device is positioned in the hollowed region of a intervertebral space or intravertebral space, the plurality of pores being sized to retain the fill material within the interior space of the substantially tubular member, the substantially tubular member including at least one fill opening through which the fill material may be introduced into the interior space, the at least one fill opening comprising at least one of the plurality of pores;

(b) inserting the substantially tubular member into the intervertebral space or intravertebral space; and (c) inserting the fill material into the interior space of the substantially tubular member through the at least one fill opening.

30. A method for stabilizing a spinal motion segment comprising the following steps: (a) providing a member constructed from a generally pliable, but minimally elastic material, the member having a first end and a second end; (b) disposing the member about the outer annulus of the intervertebral disc of a mammalian spine, the substantially tubular member having a predetermined height; and (c) securing the first end and the second end together, thereby forming the member into a substantially continuous band defining a first radius about the intervertebral disc.

31. The method of claim 30 further comprising the step of: (d) cinching at least a portion of the band to reduce the first radius and compress the disc.

* * * * *